United States Patent
An et al.

(10) Patent No.: US 9,522,934 B2
(45) Date of Patent: Dec. 20, 2016

(54) ACETATIC ABIRATERONE TRIFLUOROACETATE AND PREPARATION METHOD AND APPLICATION OF SAME

(71) Applicants: SHANGHAI CDYMAX PHARMACEUTICALS CO., LTD., Shanghai (CN); JIANGSU CDYMAX PHARMACEUTICALS CO., LTD., Qidong, Jiangsu (CN)

(72) Inventors: Xiaoxia An, Shanghai (CN); Chengjun Huang, Shanghai (CN); Fengwang Mao, Shanghai (CN)

(73) Assignees: Shanghai Cdymax Pharmaceuticals Co., Ltd., Shanghai (CN); Jiangsu Cdymax Pharmaceuticals Co., Ltd., Qidong, Jiangsu (CN); Shanghai Acebright Pharmaceuticals Group Co., Ltd., Shanghai (CN)

( * ) Notice: Subject to any disclaimer, the term of this patent is extended or adjusted under 35 U.S.C. 154(b) by 180 days.

(21) Appl. No.: 14/409,791

(22) PCT Filed: Feb. 20, 2013

(86) PCT No.: PCT/CN2013/071705
§ 371 (c)(1),
(2) Date: Dec. 19, 2014

(87) PCT Pub. No.: WO2013/123878
PCT Pub. Date: Aug. 29, 2013

(65) Prior Publication Data
US 2015/0133652 A1    May 14, 2015

(30) Foreign Application Priority Data
Feb. 21, 2012   (CN) .......................... 2012 1 0039644

(51) Int. Cl.
A61K 31/4406    (2006.01)
C07J 43/00      (2006.01)
C07C 53/10      (2006.01)

(52) U.S. Cl.
CPC .............. *C07J 43/003* (2013.01); *C07C 53/10* (2013.01)

(58) Field of Classification Search
CPC .......................... A61K 31/4406; C07J 43/003
USPC ............................................. 514/277; 540/95
See application file for complete search history.

(56) References Cited

FOREIGN PATENT DOCUMENTS

| | | |
|---|---|---|
| CN | 102030798 | 4/2011 |
| WO | 93/20097 | 10/1993 |
| WO | 95/09178 | 4/1995 |
| WO | 2006/021776 | 3/2006 |
| WO | 2006/021777 | 3/2006 |

OTHER PUBLICATIONS

International Search Report for application No. PCT/CN2013/071705, dated May 23, 2013 (4 pages).
G. A. Potter et al., "A convenient, large-scale synthesis of abiraterone acetate [3β-acetoxy-17-(3-pyridyl) androsta5,16-diene], a potential new drug for the treatment of prostate cancer," Organic Preparations and Procedures Int., vol. 29, No. 1, p. 123-128 (1997).

*Primary Examiner* — Brenda Coleman
(74) *Attorney, Agent, or Firm* — Hamre, Schumann, Mueller & Larson, P.C.

(57) ABSTRACT

Provided are acetaic abiraterone trifluoroacetate, a preparation method and an application of same. The acetaic abiraterone trifluoroacetate is obtained through a salt-forming reaction between acetaic Abiraterone and trifluoroacetic acid. The acetaic abiraterone trifluoroacetate undergoes self-purification through recrystallization, and dissociation and recrystallization are performed on the purified abiraterone acetate trifluoroacetate, so that the obtained acetaic abiraterone has a high purity, a high yield and stable quality, and is capable of meeting the requirement for mass production of acetaic abiraterone.

18 Claims, 2 Drawing Sheets

ACETATIC ABIRATERONE TRIFLUOROACETATE AND PREPARATION METHOD AND APPLICATION OF SAME

TECHNICAL FIELD

The present invention relates to abiraterone acetate trifluoroacetate and preparation method and use thereof, which belongs to the field of organic chemistry.

BACKGROUND

Abiraterone acetate (ZYTIGA) is transferred to abiraterone in vivo, which is an oral cytochrome P450 (CYP450) oxidase c17 inhibitor and inhibits synthesis of androgen by inhibiting CYP450 c17 enzyme which is a key enzyme to hormone synthesis in testis and other part of a body. On Apr. 28, 2011, US Food and Drug Administration (FDA) approved the use of abiraterone acetate (Zytiga) in combination with prednisone (steroids) in the treatment of advanced (metastatic) prostate cancer which has been treated with docetaxel (chemotherapy) and is refractory to exairesis. The chemical formula of abiraterone acetate is shown as:

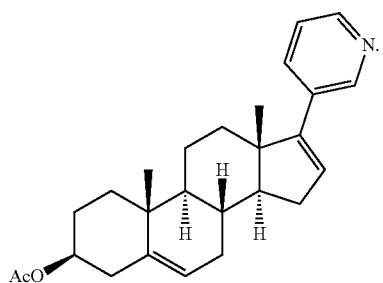

WO9320097A firstly reported this compound and its synthesis method, wherein dehydroepiandrosterone acetate as a starting material reacts with triflic anhydride to obtain dehydroepiandrosterone acetate trifluoromethanesulfonate, which then reacts with diethyl-(3-pyridyl) borane through Suzuki coupling to obtain the compound. The synthesis route is shown as follows:

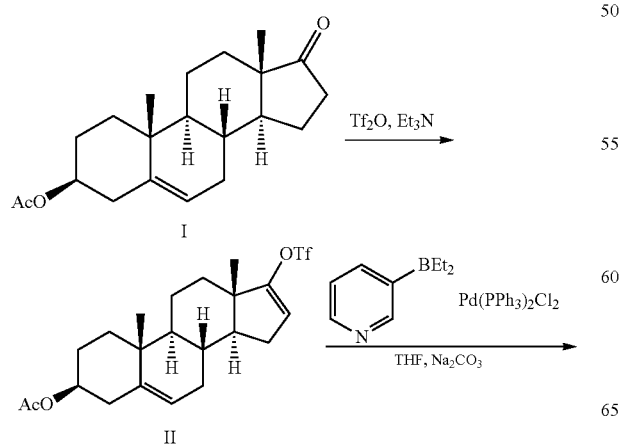

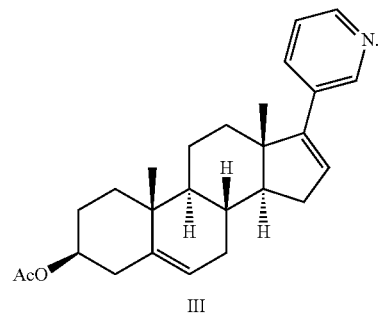

References, such as WO9509178, Org. Prep. Proced. Int, 1997, 29(1), 123-134, etc., reported another synthesis scheme for this compound:

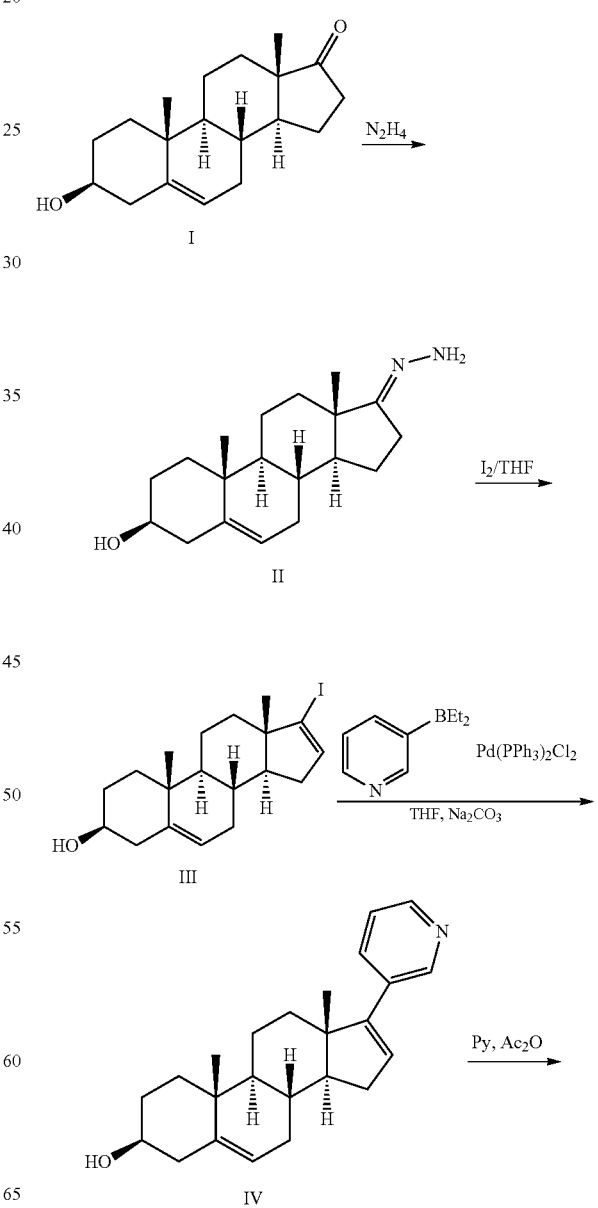

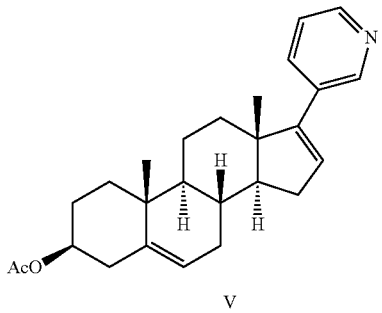

V

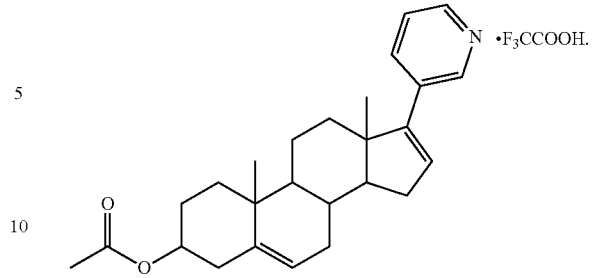

All of the above schemes require purification by column chromatography, and are not suitable for industrial manufacturing.

In WO2006021776 and WO2006021777, the same synthetic route as that in WO9320097 was used, however, in the post-processing, the crude abiraterone acetate was purified by salifying and crystallization with methanesulfonic acid, thereby removing most of the impurities including dehydroepiandrosterone acetate. But the disadvantages of this process are that upon salification of the crude abiraterone acetate, the time of filtration is pretty long, the resulting cake is viscous, impurities are prone to remain, and there are many impurities and the content of each impurity is more than 1%.

In CN102030798, the crude abiraterone acetate is purified by salifying and crystallization with trifluoromethanesulfonic acid. The difficulties in filtration is solved and the content of impurity is lower that that in WO2006021776 and WO2006021777, however, the final product is still oily, which can not meet the pharmaceutical standard by recrystallization.

In summary, the available methods for purifying abiraterone acetate have the following disadvantages: yield and purity are low; there are multiple impurities, the contents of which are high; the final product is oily; and purification through column chromatography is necessary to obtain a product meeting pharmaceutical standards; the cost is high, and it is not suitable for large-scale manufacturing.

SUMMARY OF INVENTION

Regarding the problems and defections in the prior art, the object of the present invention is to provide a abiraterone acetate trifluoroacetate and preparation method thereof and use thereof in purifying abiraterone acetate, thereby obtaining abiraterone acetate in high purity, at low cost and by simple and easy process, and meeting the requirement for scaling up the manufacture of abiraterone acetate.

In order to achieve the objects said above, the technical solution of the present invention is shown as follows.

In the first aspect of the present invention, abiraterone acetate trifluoroacetate having the following chemical formula is provided:

In another embodiment, the purity of abiraterone acetate trifluoroacetate is ≥95%, preferably, ≥98%.

In the second aspect of the present invention, a method for preparing abiraterone acetate trifluoroacetate is provided, including: salification reaction is firstly conducted for a crude abiraterone acetate with trifluoroacetic acid in an organic solvent at −5~25° C.; upon completion, the mixture is filtered; and the filter cake is washed so as to obtain abiraterone acetate trifluoroacetate.

In another embodiment, the method for preparing abiraterone acetate trifluoroacetate includes: salification reaction is firstly conducted for a crude abiraterone acetate with trifluoroacetic acid in an organic solvent at −5~25° C.; upon completion, the mixture is filtered; and the filter cake is washed, so as to obtain abiraterone acetate trifluoroacetate as a earthy yellow solid.

In another embodiment, the filter cake is washed with the organic solvent used in the salification reaction.

As a preferable embodiment, the organic solvent is an ester solvent and/or an ether solvent, the ester solvent is formed by $C_1$-$C_4$ acid and $C_1$-$C_4$ alcohol, and the ether solvent is formed by $C_1$-$C_4$ alcohol and $C_1$-$C_4$ alcohol.

As a preferable embodiment, the organic solvent is a mixture of an ester solvent and an ether solvent, the ester solvent is formed by $C_1$-$C_4$ acid and $C_1$-$C_4$ alcohol, and the ether solvent is formed by $C_1$-$C_4$ alcohol and $C_1$-$C_4$ alcohol.

As a further preferable embodiment, the organic solvent is a mixture of ethyl acetate and tert-butyl methyl ether in a volume ratio of 1:2~2:1.

As a most preferable embodiment, the organic solvent is a mixture of ethyl acetate and tert-butyl methyl ether in a volume ratio of 2:3.

As a preferable embodiment, the mole ratio of trifluoroacetic acid and abiraterone acetate is 0.8:1~1.4:1.

As a further preferable embodiment, the mole ratio of trifluoroacetic acid and abiraterone acetate is 1:1~1.2:1.

As a preferable embodiment, the salification reaction is conducted at −5~5° C. for 0.5 h firstly, and then at 5~25° C. for another 1 h.

In the third aspect of the present invention, a use of abiraterone acetate trifluoroacetate of the first aspect for purifying abiraterone acetate is provided.

In another embodiment, the method for purifying abiraterone acetate using abiraterone acetate trifluoroacetate comprises the following steps:

a) Recrystallizing the obtained abiraterone acetate trifluoroacetate in C1~C4 alcohol, b) Neutralizing the recrystallized abiraterone acetate trifluoroacetate by a base, obtaining a free abiraterone acetate, c) Recrystallizing the free abiraterone acetate in an organic solvent.

As a preferable embodiment, abiraterone acetate trifluoroacetate is recrystallized in isopropyl, and the volume of isopropyl is 10~15 times based on the weight of abiraterone acetate trifluoroacetate.

As a preferable embodiment, in step b), water-insoluble solvent, ester, ether or halohydrocarbon, is needed, preferably, dichloromethane.

As a preferable embodiment, in step b), pH of aqueous phase is controlled at >10.

As a preferable embodiment, the base used in step b) is an aqueous solution of sodium carbonate or potassium carbonate, preferably, an aqueous solution of sodium carbonate with weight percent concentration of 20±10%.

As a preferable embodiment, in step c), the organic solvent is one or more of solvents selected from acetonitrile, ethyl acetate, isopropyl acetate, n-hexane, and cyclohexane.

As a preferable embodiment, in step c), the organic solvent is acetonitrile, and the volume of acetonitrile is 3~6 times based on the weight of abiraterone acetate.

In the fourth aspect of the invention, a method for purifying abiraterone acetate is provided, comprising steps of:

a) Recrystallizing abiraterone acetate trifluoroacetate of the first aspect in C1~C4 alcohol, b) Neutralizing the recrystallized abiraterone acetate trifluoroacetate by a base, so as to obtain a free abiraterone acetate, c) Recrystallizing the free abiraterone acetate in an organic solvent.

In a preferable embodiment, abiraterone acetate trifluoroacetate is recrystallized in isopropyl, and the volume of isopropyl is 10~15 times based on the weight of abiraterone acetate trifluoroacetate.

In a preferable embodiment, in step b), water-insoluble solvent, ester, ether or halohydrocarbon, is needed, preferably, dichloromethane.

In a preferable embodiment, in step b), pH of aqueous phase is controlled at >10.

In a preferable embodiment, in step b), the base is an aqueous solution of sodium carbonate or potassium carbonate, preferably, an aqueous solution of sodium carbonate with weight percent concentration of 20±10%.

In a preferable embodiment, in step b), the organic solvent is one or more solvents selected from acetonitrile, ethyl acetate, isopropyl acetate, n-hexane, and cyclohexane.

In a preferable embodiment, in step c), the organic solvent is acetonitrile, and the volume of acetonitrile is 3~6 times based on the weight of abiraterone acetate.

In the fifth aspect of the present invention, a purified abiraterone acetate is provided, the purity of which is ≥98%, preferably, ≥99.5%.

In another embodiment, the content of each impurity in the purified abiraterone acetate is <0.5%.

Compared with the prior art, the abiraterone acetate trifluoroacetate of the present invention is a solid and can be purified by recrystallization. Abiraterone acetate which meets the pharmaceutical standards is easily obtained by dissociating and recrystallizing the resulting purified abiraterone acetate trifluoroacetate, wherein the purity of abiraterone acetate is more than 99.5% and the content of a single impurity is less than 0.1%. The present invention overcomes the defect in the prior art that column chromatography is necessary for purifying abiraterone acetate, and has the following advantages that the salification reagents are cheap, the salification and purification process is simple and easy, the yield is high and the quality is stable, thereby obtaining abiraterone acetate with high purity at low cost and by simple and easy process, and meeting the requirement for mass production of abiraterone acetate.

It should be understood that in the present invention, any of the technical features specifically described above and below (such as in the Examples) can be combined with each other, thereby constituting new or preferred technical solutions that are not described one by one in the specification.

DETAILED DESCRIPTION OF INVENTION

The invention will be further illustrated in detail with reference to the following embodiments.

The crude abiraterone acetate described in examples is prepared according to the method in WO2006021776 or WO2006021777: dehydroepiandrosterone acetate trifluoromethanesulfate is obtained by reacting dehydroepiandrosterone acetate as a starting material with trifluoromethanesulfonic anhydride, wherein triethylamine is used as a base; and the crude abiraterone acetate is obtained by reacting dehydroepiandrosterone acetate trifluoromethanesulfate with diethyl-(3-pyridyl) borane through Suzuki coupling; and the resulting crude abiraterone acetate is a brownish black foamy solid with a purity of 75%, wherein the maximum impurity is the starting material, dehydroepiandrosterone acetate.

Example 1

Preparation of Abiraterone Acetate Trifluoroacetate

Figure 1:
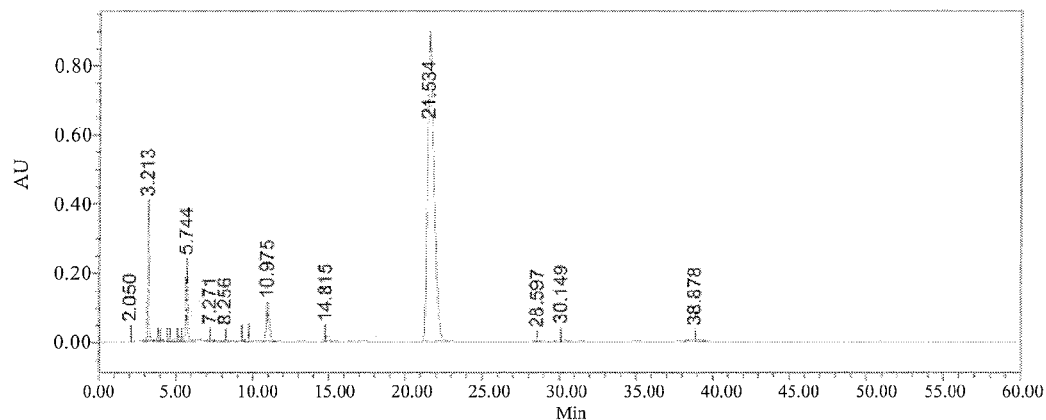
FIG. 1 shows the abiraterone acetate prepared in step ① of example 1.

① Preparation of Crude Abiraterone Acetate a) Into a 1 L dry four-necked bottle was added 33 g of dehydroepiandrosterone acetate, and then vacuumized under argon. 400 ml of dichloromethane was added. The mixture was stirred till dissolved. The temperature was controlled at 0~30° C. and 23.5 mL of trifluoromethanesulfonic anhydride was added dropwise over 10~20 minutes. Upon addition, the mixture was stirred for 10 min at an inner temperature of 0~30° C. Then 200 mL of triethylamine solution in dichloromethane was added dropwise at 0~30° C. over 35~40 minutes. Upon addition, the mixture was stirred for 1 hour at an inner temperature for 0~30° C. and the reaction was monitored by thin-layer chromatography (TLC). The reaction was quenched by adding 250 mL of ice-water, 250 mL of dichloromethane was added, layers were separated, the dichloromethane phase was collected and the aqueous phase was extracted twice with 100 mL of dichloromethane. The combined dichloromethane phases were washed with 250 mL of 1 g/L HCl and 250 mL of saturated aqueous sodium chloride. The dichloromethane phases were collected, dried over anhydrous sodium sulfate, and decolorized by 10 g of activated carbon. The mixture was stirred at room temperature for 1 hour, and then filtered with diatomite. The filtrate was concentrated to obtain 47.3 g of brownish black oil.

b) Into a reaction bottle was added 0.42 g of bis(triphenylphosphine)palladium(II) chloride and 14.7 g of diethyl-(3-pyridyl) borane, and then vacuumized under argon. 47.3 g of brownish black oil obtained in step a) was dissolved in 400 mL of tetrahydrofuran, and the tetrahydrofuran solution was added into the aforesaid reaction bottle. The mixture was stirred at room temperature for 5 min, and then 225 mL of 17 wt % aqueous solution of sodium carbonate was added and stirred for another 5 min at room temperature. After that, the bottle was placed in an oil-bath, and the reaction was refluxed for 4~5 hours. The reaction was monitored by TLC till the conversion was complete. The reaction mixture was cooled to room temperature, 400 mL of ethyl acetate and 400 mL of water were added, and layers were separated. The ethyl acetate phase was collected and the aqueous phase was extracted twice with 200 mL of ethyl acetate. The ethyl acetate phases were combined, dried over anhydrous sodium sulfate and then filtered by suction. The filtrate was concentrated to obtain 44.2 g of brownish black oil. 145 mL of methanol was added into the obtained 44.2 g of brownish black oil and then warmed gently by hair drier till the oil was dissolved. The solution was standing at room temperature and great amount of solids precipitated. After 2 hours, the mixture was filtered by suction. The filtrate was washed with a little ice methanol and concentrated to obtain 41.4 g of brownish black foamy solid, i.e. crude abiraterone acetate, in HPLC purity of 75.29%. See FIG. 1 and table 1 (processing channel: W2498ChA 210 nm).

TABLE 1

|  | retention time (min) | % Area |
| --- | --- | --- |
| 1 | 2.050 | 0.3362 |
| 2 | 3.213 | 6.8640 |
| 3 | 3.833 | 0.4866 |
| 4 | 3.893 | 0.8317 |
| 5 | 4.063 | 0.1841 |
| 6 | 4.461 | 0.4627 |
| 7 | 4.613 | 0.3372 |
| 8 | 5.120 | 0.9873 |
| 9 | 5.419 | 0.3991 |
| 10 | 5.744 | 5.0677 |
| 11 | 7.271 | 0.2500 |
| 12 | 8.256 | 0.1529 |
| 13 | 9.306 | 0.7059 |
| 14 | 9.725 | 0.7975 |
| 15 | 10.975 | 3.8030 |
| 16 | 14.815 | 0.8512 |
| 17 | 21.534 | 75.2946 |
| 18 | 28.597 | 0.1493 |
| 19 | 30.149 | 1.1986 |
| 20 | 38.878 | 0.8406 |

Figure 2:
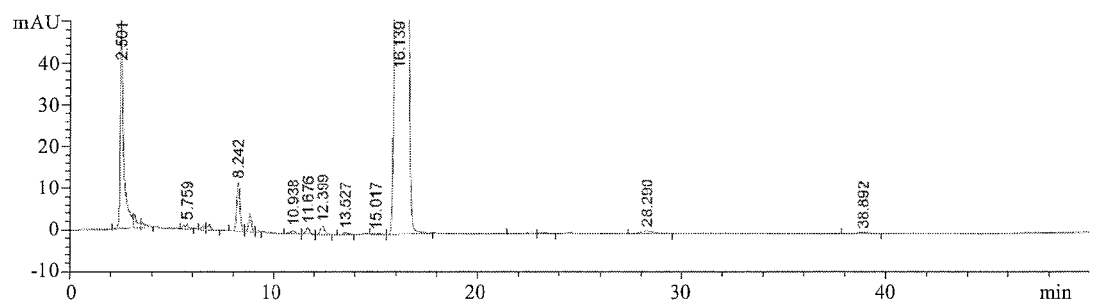
FIG. 2 shows the abiraterone acetate trifluoroacetate prepared in step ② of example 1.

② Preparing Abiraterone Acetate Trifluoroacetate 41.4 g of crude abiraterone acetate obtained in step ①, 125 mL of ethyl acetate and 125 mL of methyl tert-butyl ether were added in a dry 1 L four-necked bottle. The mixture was stirred till dissolved. The mixture was cooled to −5~5° C. in an ice-salt bath, and then 7.8 mL of trifluoroacetic acid was added dropwise over 5~10 min. Upon addition, the mixture was reacted at −5~5° C. for 0.5 h, the ice-salt bath was removed and the mixture was reacted at room temperature (about 20~25° C.) for another 1 h. Then the mixture was filtered by suction. The filter cake was washed with 50 mL of methyl tert-butyl ether and dried by suction to obtain 28.1 g of earthy-yellow solids, i.e. abiraterone acetate trifluoroacetate, in a weight yield of 67.8% and HPLC purity of 95.15%. See FIG. 2 and table 2 (signal: VWD1 A, wavelength, 215 nm).

HNMR (DMSO, δppm): 8.82-8.7 (d, 1H), 8.67-8.55 (d, 1H), 8.24-8.11 (d, 1H), 7.76-7.6 (dd, 1H), 6.42-6.26 (s, 1H), 5.48-5.35 (d, 1H), 4.60-4.36 (d, 1H), 2.37-2.20 (m, 3H), 2.17-1.95 (m, 6H), 1.90-1.35 (m, 9H), 1.34-0.95 (m, 9H);

Specific rotation: −38.1674°; melting point: 185° C.-187.1° C.; content of fluoro: 11.03%.

TABLE 2

| Peak # | retention time [min] | peak area % |
| --- | --- | --- |
| 1 | 2.501 | 2.7927 |
| 2 | 3.205 | 0.1712 |
| 3 | 3.566 | 0.0789 |
| 4 | 5.759 | 0.0920 |
| 5 | 6.520 | 0.0600 |
| 6 | 6.859 | 0.0742 |
| 7 | 8.242 | 0.6490 |
| 8 | 8.815 | 0.2462 |
| 9 | 9.217 | 0.0267 |
| 10 | 10.938 | 0.0743 |
| 11 | 11.676 | 0.1035 |
| 12 | 12.399 | 0.1572 |
| 13 | 13.527 | 0.0358 |
| 14 | 15.017 | 0.0354 |
| 15 | 16.139 | 95.1579 |
| 16 | 22.647 | 0.0466 |
| 17 | 23.085 | 0.0337 |
| 18 | 28.290 | 0.1256 |
| 19 | 38.892 | 0.0392 |

Example 2

Preparation of Abiraterone Acetate Trifluoroacetate 16.6 g of crude abiraterone acetate and 40 mL of isopropyl acetate and 60 mL of isopropyl ether were added in a dry 250 mL four-necked bottle. The mixture was stirred till dissolved. The mixture was cooled to −5~5° C. in an ice-salt bath, and then 2.5 mL of trifluoroacetic acid was added dropwise over 5~10 min. Upon addition, the mixture was reacted at −5~5° C. for 0.5 h, the ice-salt bath was removed and the mixture was reacted at room temperature (about 20~25° C.) for another 1 h. The mixture was filtered. The filter cake was washed with 10 mL of isopropyl ether and dried by suction to obtain 10.9 g of earthy-yellow solids, i.e. abiraterone acetate trifluoroacetate in a weight yield of 65.6% and HPLC purity of 96.33%. HNMR is substantially identical to that of example 1.

Example 3

Preparation of Abiraterone Acetate Trifluoroacetate 12.4 g of crude abiraterone acetate and 45 mL of isopropyl acetate and 30 mL of methyl tert-butyl ether were added in a dry 250 mL four-necked bottle. The mixture was stirred till dissolved. The mixture was cooled to −5~5° C. in an ice-salt bath, and then 9.3 mL of trifluoroacetic acid was added dropwise over 5~10 min. Upon addition, the mixture was reacted at −5~5° C. for 0.5 h, the ice-salt bath was removed, and the mixture was reacted at room temperature (about 20~25° C.) for another 1 h. The mixture was filtered. The filter cake was washed with 10 mL of methyl tert-butyl ether and dried by suction to obtain 8.3 g of earthy-yellow solids, i.e. abiraterone acetate trifluoroacetate in a weight yield of 66.9% and HPLC purity of 95.73%. HNMR is substantially identical to that of example 1.

Example 4

Figure 3:
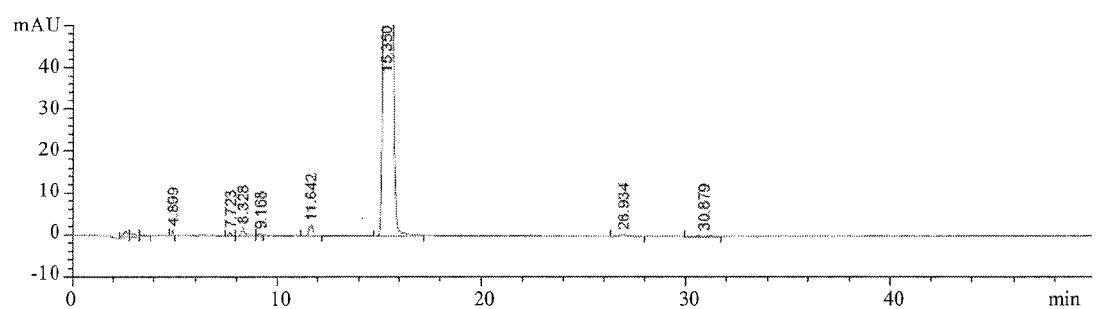
FIG. 3 shows the abiraterone acetate trifluoroacetate prepared in step a) of example 4.

Purification of Abiraterone Acetate a) 28.1 g of abiraterone acetate trifluoroacetate prepared in example 1 was transferred into a 500 mL one-necked bottle, into which was added 300 mL of isopropanol. The mixture was heated to reflux, cooled to room temperature after being dissolved, and then filtered by suction. The filter cake was washed with a little ice isopropanol and dried in an oven to obtain 21.66 g of pale yellow solids, i.e., purified abiraterone acetate trifluoroacetate in a weight yield of 77.1% and HPLC purity of 98.49%. See FIG. 3 and table 3 (signal: VWD1 A, wavelength 215 nm).

TABLE 3

Figure 4:
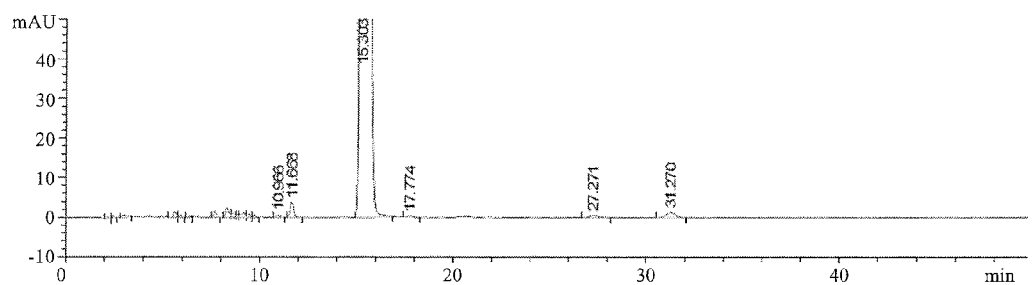
FIG. 4 shows the abiraterone acetate prepared in step b) of example 4.

| Peak # | retention time [min] | peak area % |
|---|---|---|
| 1 | 2.602 | 0.2385 |
| 2 | 2.989 | 0.1535 |
| 3 | 3.466 | 0.0509 |
| 4 | 4.899 | 0.0703 |
| 5 | 7.723 | 0.0776 |
| 6 | 8.328 | 0.2863 |
| 7 | 9.168 | 0.0667 |
| 8 | 11.642 | 0.3526 |
| 9 | 15.350 | 98.4930 |
| 10 | 26.934 | 0.1189 |
| 11 | 30.879 | 0.0918 | b) 21.66 g of the above pale yellow solids were added into 200 mL of dichloromethane. The mixture was stirred till substantially dissolved, and then 20 wt % aqueous solution of sodium carbonate was added. pH of the aqueous solution was controlled at >10. The mixture was stirred at room temperature for 1 h and layers were separated. The aqueous layer was extracted with 100 mL of dichloromethane twice. The dichloromethane layers were combined, dried over anhydrous sodium sulphate, and filtered by suction. The filtrate was concentrated to obtain 16.55 g of pale yellow solids, i.e. free abiraterone acetate in a HPLC purity of 99.09% and the content of each single impurity of less than 0.2%. See FIG. 4 and table 4 (signal: VWD1 A, wavelength 215 nm), in a weight yield of 76.4%.

TABLE 4

Figure 5:
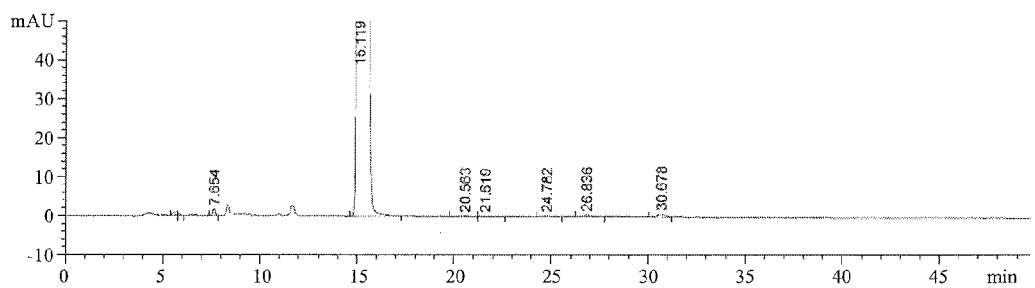
FIG. 5 shows the abiraterone acetate prepared in step c) of example 4.

| Peak # | retention time [min] | peak area % |
|---|---|---|
| 1 | 2.234 | 0.0178 |
| 2 | 2.409 | 0.0108 |
| 3 | 2.970 | 0.0356 |
| 4 | 5.608 | 0.0524 |
| 5 | 5.901 | 0.0155 |
| 6 | 6.410 | 0.0103 |
| 7 | 7.694 | 0.0521 |
| 8 | 8.328 | 0.0950 |
| 9 | 8.614 | 0.0424 |
| 10 | 8.833 | 0.0249 |
| 11 | 9.196 | 0.0691 |
| 12 | 9.441 | 0.0334 |
| 13 | 9.736 | 0.0161 |
| 14 | 10.966 | 0.0276 |
| 15 | 11.668 | 0.1731 |
| 16 | 15.303 | 99.0936 |
| 17 | 17.774 | 0.0175 |
| 18 | 27.271 | 0.0702 |
| 19 | 31.270 | 0.1424 | c) 16.55 g of the pale yellow solids obtained above was added into 80 mL of acetonitrile. The mixture was refluxed till dissolved, then cooled to room temperature and filtered. The filter cake was washed with 5 mL of ice acetonitrile and dried in an oven to obtain 15.05 g of product in a HPLC purity of 99.74% and the content of each single impurity of less than 0.1%. See FIG. 5 and table 5 (signal: VWD1 A, wavelength 215 nm), the product can meet the medicinal standards for abiraterone acetate.

TABLE 5

| Peak # | retention time [min] | peak area % |
|---|---|---|
| 1 | 5.574 | 0.0281 |
| 2 | 5.867 | 0.0130 |
| 3 | 7.654 | 0.0497 |
| 4 | 15.119 | 99.7409 |
| 5 | 20.563 | 0.0182 |
| 6 | 21.619 | 0.0138 |
| 7 | 24.782 | 0.0166 |
| 8 | 26.836 | 0.0514 |
| 9 | 30.678 | 0.0683 |

Example 5

5.0 g of the free crude abiraterone acetate as pale yellow solids obtained in step b) of example 4 were added into 40 mL of ethyl acetate. The mixture was heated to reflux till dissolved, then slowly cooled to 0~5° C. and filtered. The filter cake was washed with 5 mL of ice ethyl acetate and dried in an oven to obtain 4.18 g of product in a HPLC purity of 99.51% and content of each single impurity of less than 0.1%, thereby obtaining abiraterone acetate meeting the medicinal standards.

Example 6

5.0 g of the free crude abiraterone acetate as pale yellow solids obtained in step b) of example 4 were added into a mixture of 30 mL of acetonitrile and 20 mL of n-hexane. The mixture was heated to reflux till dissolved, then slowly cooled to 0~5° C. and filtered. The filter cake was washed with 5 mL of ice acetonitrile and dried in an oven to obtain 4.09 g of product in a HPLC purity of 99.67% and content of each single impurity of less than 0.1%, thereby obtaining abiraterone acetate meeting the medicinal standards.

Example 7

5.0 g of the free crude abiraterone acetate as pale yellow solids obtained in step b) of example 4 was added into a mixture of 20 mL of acetonitrile and 20 mL of isopropyl acetate. The mixture was heated to reflux till dissolved, then slowly cooled to 0~5° C. and filtered. The filter cake was washed with 5 mL of ice acetonitrile and dried in an oven to obtain 4.11 g of product in a HPLC purity of 99.83% and content of each single impurity of less than 0.1%, thereby obtaining abiraterone acetate meeting the medicinal standards.

Comparison of the quality of free abiraterone acetate obtained in this example and that obtained according to the method disclosed in WO2006021777 and CN102030798 was shown in table 6.

TABLE 6

| Sample | Example 4 | WO2006021777 | CN102030798 |
|---|---|---|---|
| Form | pale yellow solid | brownish black oil | brownish black oil |
| Total yield | 50.15% | 42.18% | 41.81% |
| HPLC purity | 99.09% | 93.58% | 97.44% |

TABLE 6-continued

| Sample | Example 4 | WO2006021777 | CN102030798 |
|---|---|---|---|
| Related impurity | no impurity in a content of more than 1% | 4 impurities in a content of more than 1% | 1 impurity in a content of more than 1% |

As shown in table 1, compared with the prior art, abiraterone acetate can be purified by using abiraterone acetate trifluoroacetate provided in the present invention in high yield, high purity and less impurity. Abiraterone acetate meeting the pharmaceutical standards can be obtained by merely using recrystallization, and abiraterone acetate in high purity can be obtained at low cost and by using simple and easy process, thereby meeting the requirements for mass production of abiraterone acetate.

Finally, it is necessary to point out that the above content is only a further explanation of the invention, and can not be understood as limiting the protection range of the invention. Some non essential improvements and adjustments of the above content by the skilled in the art belong to the invention.

All literatures mentioned in the present application are incorporated by reference herein, as though individually incorporated by reference. Additionally, it should be understood that after reading the above teaching, many variations and modifications may be made by the skilled in the art, and these equivalents also fall within the scope as defined by the appended claims.

What we claim is:

1. An abiraterone acetate trifluoroacetate, having the following chemical formula:

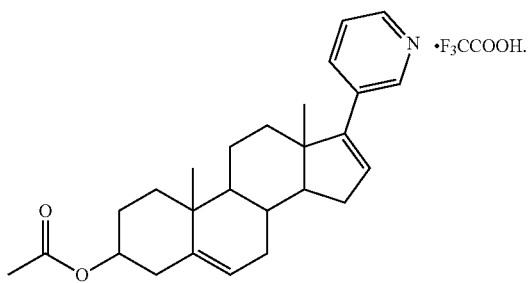 [SMILES: CC(=O)OC1CCC2(C)C(=CCC3C2CCC2(C)C(c4cccnc4)=CCC32)C1]

2. A method for preparing the abiraterone acetate trifluoroacetate according to claim 1, wherein the method comprises the following steps: salification reaction is firstly conducted for a crude abiraterone acetate with trifluoroacetic acid in an organic solvent at −5~25° C.; upon completion, the mixture is filtered; and the filter cake is washed so as to obtain abiraterone acetate trifluoroacetate.

3. The method for preparing the abiraterone acetate trifluoroacetate of claim 2, wherein the organic solvent is an ester solvent and/or an ether solvent, the ester solvent is formed by $C_1$-$C_4$ acid and $C_1$-$C_4$ alcohol, and the ether solvent is formed by $C_1$-$C_4$ alcohol and $C_1$-$C_4$ alcohol.

4. The method for preparing the abiraterone acetate trifluoroacetate of claim 3, wherein the organic solvent is a mixture of an ester solvent and an ether solvent, the ester solvent is formed by $C_1$-$C_4$ acid and $C_1$-$C_4$ alcohol, and the ether solvent is formed by $C_1$-$C_4$ alcohol and $C_1$-$C_4$ alcohol.

5. The method for preparing the abiraterone acetate trifluoroacetate of claim 4, wherein the organic solvent is a mixture of ethyl acetate and tert-butyl methyl ether in a volume ratio of 1:2~2:1.

6. The method for preparing the abiraterone acetate trifluoroacetate of claim 4, wherein the organic solvent is a mixture of ethyl acetate and tert-butyl methyl ether in a volume ratio of 2:3.

7. The method for preparing the abiraterone acetate trifluoroacetate of claim 2, wherein the mole ratio of trifluoroacetic acid and abiraterone acetate is 0.8:1~1.4:1.

8. The method for preparing the abiraterone acetate trifluoroacetate of claim 2, wherein the mole ratio of trifluoroacetic acid and abiraterone acetate is 1:1~1.2:1.

9. The method for preparing the abiraterone acetate trifluoroacetate of claim 2, wherein the salification reaction is conducted at −5~5° C. for 0.5 h firstly, and then at 5~25° C. for another 1 h.

10. A method for preparing abiraterone acetate from the abiraterone acetate trifluoroacetate of claim 1, comprising:
   a) crystallizing the abiraterone acetate trifluoroacetate of claim 1 in C1~C4 alcohol to obtain a crystallized abiraterone acetate trifluoroacetate,
   b) neutralizing the crystallized abiraterone acetate trifluoroacetate using a aqueous solution of a base and obtaining a free crude abiraterone acetate, and
   c) crystallizing the free crude abiraterone acetate in an organic solvent.

11. The method of claim 10, wherein, in step a), the abiraterone acetate trifluoroacetate of claim 1 is crystallized in isopropyl alcohol, a volume value of the isopropyl alcohol being in a unit of milliliter is 10~15 times a weight value of the abiraterone acetate trifluoroacetate of claim 1 being in a unit of gram.

12. The method of claim 10, wherein obtaining the free crude abiraterone acetate in step b) comprising extracting a aqueous layer obtained from neutralizing the crystallized abiraterone acetate trifluoroacetate using a water-insoluble solvent, ester, ether or halohydrocarbon.

13. The method of claim 10, wherein, in step b), the aqueous solution has a pH value of >10.

14. The method of claim 10, wherein the aqueous solution of the base used in step b) is an aqueous solution of sodium carbonate or potassium carbonate.

15. The method of claim 10, wherein, in step c), the organic solvent is one or more solvents selected from acetonitrile, ethyl acetate, isopropyl acetate, n-hexane, and cyclohexane.

16. The method of claim 10, wherein, in step c), the organic solvent is acetonitrile, and a volume value of the acetonitrile being in a unit of milliliter is 3~6 times a weight value of the free abiraterone acetate being in a unit of gram.

17. The method of claim 10, wherein the purified abiraterone acetate has a purity of ≥98%.

18. A purified abiraterone acetate, wherein the purity of the purified abiraterone acetate is ≥98%, the purified abiraterone acetate being purified from the abiraterone acetate trifluoroacetate of claim 1, the purified abiraterone being prepared by a method comprising:
   a) crystallizing the abiraterone acetate trifluoroacetate of claim 1 in C1~C4 alcohol to obtain a crystallized abiraterone acetate trifluoroacetate,
   b) neutralizing the crystallized abiraterone acetate trifluoroacetate using a base and obtaining a free crude abiraterone acetate, and
   c) crystallizing the free crude abiraterone acetate in an organic solvent.

* * * * *